United States Patent [19]

Farge et al.

[11] 4,363,909
[45] Dec. 14, 1982

[54] THIAZOLO[3,4-b]ISOQUINOLINES

[75] Inventors: Daniel Farge, Thiais; Alain Jossin, St-Cloud; Gerard Ponsinet, Sucy-en Brie; Daniel Reisdorf, Thiais, all of France

[73] Assignee: Rhone Poulenc Industries, France

[21] Appl. No.: 212,253

[22] Filed: Dec. 2, 1980

[30] Foreign Application Priority Data

Dec. 4, 1979 [FR] France .................. 79 29751
Oct. 17, 1980 [FR] France .................. 80 22260

[51] Int. Cl.³ .......................................... C07D 513/04
[52] U.S. Cl. ..................... 544/238; 424/250; 424/251; 424/258; 544/323; 544/328; 544/331; 544/405; 546/80
[58] Field of Search ............... 546/80; 544/238, 323, 544/328, 331, 405; 424/250, 251, 258

[56] References Cited

U.S. PATENT DOCUMENTS 4,064,247 12/1977 Farge et al. ................ 546/80 X
4,153,698 5/1979 Farge et al. ................ 546/80 X

FOREIGN PATENT DOCUMENTS 2802453 7/1978 Fed. Rep. of Germany .

OTHER PUBLICATIONS

De Long, D., et al., *J. Infectious Diseases*, 141(1), 87 (1980).
Reed, S., et al., *J. Infectious Diseases*, 133 (Supp), A128 (1976).
Phillpotts, R., et al., *The Lancet*, 1342 (1981).

*Primary Examiner*—Richard A. Schwartz
*Attorney, Agent, or Firm*—Stevens, Davis, Miller & Mosher

[57] ABSTRACT

Isoquinoline derivatives of the formula

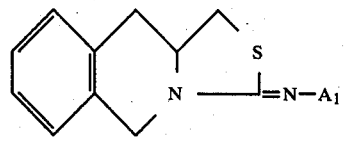

wherein the symbol $A_1$ represents an isoquinol-8-yl, 3-methylisoquinol-8-yl, 3-hydroxymethylisoquinol-5-yl, 3-carboxymethylisoquinol-5-yl, quinol-5-yl, thienopyridyl, benzimidazolyl, thienyl or thiazolyl radical, a 4-(or 5-)carboxyalkylthiazol-2-yl radical in which the alkyl moiety is linear or branched and contains 1 to 4 carbon atoms, or a 1,3,4-thiadiazol-2-yl, pyrazolyl, imidazolyl, pyrimidinyl, pyridazinyl or pyrazinyl radical, monocyclic heterocyclic rings within the definition of $A_1$ being optionally substituted by a linear or branched alkyl radical containing 1 to 4 carbon atoms, in the (S) or (R,S) form or mixtures thereof, and salts thereof possess useful pharmocological properties, in particular antiviral activity.

10 Claims, No Drawings

THIAZOLO[3,4-b]ISOQUINOLINES

This invention relates to new isoquinoline derivatives, to processes for their preparation and to compositions containing them.

In the specifications of our British Pat. No. 1,503,091 and Belgian Pat. No. 844,927 we have described and claimed thiazolo[3,4-b]isoquinolines of the general formula:

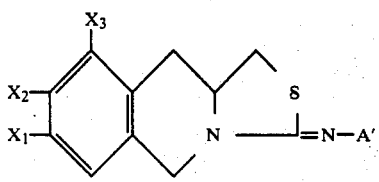

wherein A' represents pyrid-3- or -4-yl or isoquinol-5-yl and $X_1$, $X_2$ and $X_3$ represents, inter alia, hydrogen atoms. These compounds possess analgesic and antipyretic activity.

In the specifications of our British Pat. No. 1,574,281 and Belgian Pat. No. 863,083 we have described and claimed thiazolo[3,4-b]isoquinolines of the general formula:

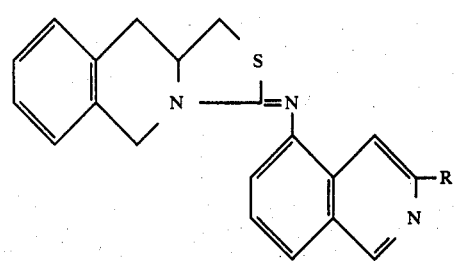

wherein R is an alkyl radical containing 1 to 10 carbon atoms which possess analgesic, anti-inflammatory and antipyretic activity.

It has now been found that certain new isoquinoline derivatives possess useful pharmacological properties, in particular anti-viral activity.

The present invention accordingly provides new thiazolo[3,4-b]isoquinoline derivatives of the general formula:

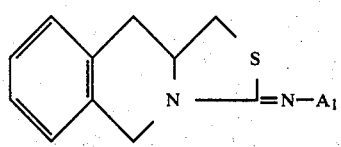

wherein the symbol $A_1$ represents an isoquinol-8-yl, 3-methylisoquinol-8-yl, 3-hydroxymethylisoquinol-5-yl, 3-carboxymethylisoquinol-5-yl, quinol-5-yl, thienopyridyl, benzimidazolyl, thienyl or thiazolyl radical, a 4-(or 5-)carboxyalkylthiazol-2-yl radical in which the alkyl moiety is linear or branched and contains 1 to 4 carbon atoms, or a 1,3,4-thiadiazol-2-yl, pyrazolyl, imidazolyl, pyrimidinyl, pyridazinyl or pyrazinyl radical, it being understood that monocyclic heterocyclic rings within the definition of $A_1$ may be substituted by a linear or branched alkyl radical containing 1 to 4 carbon atoms, in the (S) or (R,S) form or mixtures thereof, and, when $A_1$ is other than thienyl, acid addition salts thereof and, when $A_1$ represents a 3-carboxymethylisoquinol-5-yl or 4-(or 5-)carboxyalkylthiazol-2-yl radical optionally substituted by an alkyl radical as hereinbefore defined, metal salts thereof and addition salts with nitrogen-containing bases.

According to a feature of the invention, the compounds of general formula III can be obtained by the process which comprises reacting an amine of the general formula:

$$A_1-NH_2 \qquad IV$$

(wherein $A_1$ is as hereinbefore defined) with a salt of the general formula:

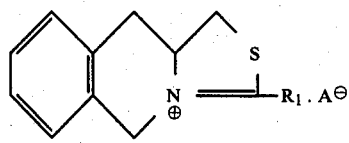

wherein $R_1$ represents a chlorine atom and $A^\ominus$ represents a chloride ion or $R_1$ represents an alkylthio radical containing 1 to 4 carbon atoms (preferably methylthio) or a benzylthio radical and $A^\ominus$ represents an iodide, sulphate, tetrafluoroborate or fluorosulphonate ion. The reaction is generally carried out in a basic medium at a temperature of 15° to 50° C.

When $R_1$ represents a chlorine atom and $A^\ominus$ represents a chloride ion, the reaction is preferably carried out in an organic solvent, such as acetonitrile, in the presence of a base, such as triethylamine.

When $R_1$ represents an alkylthio or benzylthio radical and $A^\ominus$ represents an iodide, sulphate, tetrafluoroborate or fluorosulphonate ion, the reaction is preferably carried out in a basic organic solvent, such as pyridine.

The salt of general formula V can be prepared in accordance with the method described in Belgian Pat. No. 844,927 and British Pat. No. 1,503,091.

The amines of general formula IV are prepared in accordance with, or by adaptation of, the methods described hereinafter in the Examples.

According to a further feature of the invention, the isoquinoline derivatives of general formula III wherein $A_1$ represents an isoquinol-8-yl, 3-methylisoquinol-8-yl, 3-hydroxymethylisoquinol-5-yl, 3-carboxymethylisoquinol-5-yl, thienopyridyl, benzimidazol-5(or -6)-yl or quinol-5-yl radical, or a pyrimidin-2-yl or thien-2-yl radical optionally substituted by an alkyl radical can also be obtained by the process which comprises the cyclisation in an acid medium of a 1,2,3,4-tetrahydroisoquinoline of the general formula:

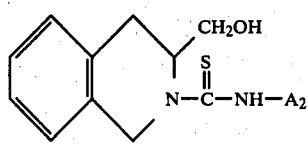

wherein $A_2$ represents an isoquinol-8-yl, 3-methylisoquinol-8-yl, 3-hydroxymethylisoquinol-5-yl, 3-carboxymethylisoquinol-5-yl, thienopyridyl, benzimidazol-5(or -6)yl or quinol-5-yl radical, or a pyrimidin-2-yl or thien-2-yl radical optionally substituted by a linear or branched alkyl radical containing 1 to 4 carbon atoms.

The cyclisation is generally carried out by heating in an acid medium. It is particularly advantageous to carry out the reaction at a temperature between 65° C. and the reflux temperature of the reaction mixture, in an aqueous solution of an inorganic acid, e.g. in hydrochloric acid (preferably 4 N to 8 N).

The 1,2,3,4-tetrahydroisoquinolines of general formula VI can be obtained by reacting an isothiocyanate of the general formula:

$$S=C=N-A_2 \qquad \text{VII}$$

wherein $A_2$ is as hereinbefore defined, with 3-hydroxymethyl-1,2,3,4-tetrahydroisoquinoline.

The reaction is generally carried out in an organic solvent, such as an alcohol, e.g. ethanol, at a temperature between 0° and 50° C.

3-Hydroxymethyl-1,2,3,4-tetrahydroisoquinoline can be prepared from phenylalanine in accordance with the method described by S. Yamada and T. Kunieda, Chem. Pharm. Bull., 15, 490 (1967).

When L-phenylalanine is used, the product of the general formula III is obtained in the (S) form.

When D,L-phenylalanine is used, the product of general formula III is obtained in the (R,S) form [i.e. an equimolecular mixture of the (R) and (S) forms].

The isothiocyanates of general formula VII, wherein $A_2$ is as hereinbefore defined except that it does not represent pyrimidin-2-yl or thien-2-yl optionally substituted by an alkyl radical, can be obtained by condensation of carbon disulphide with an amine of the general formula $A_2-NH_2$ wherein $A_2$ is as hereinbefore defined, followed by the addition of dicyclohexylcarbodiimide.

The condensation is generally carried out in the presence of a base, such as a tertiary amine, e.g. triethylamine. The reaction is advantageously carried out in an organic solvent, such as pyridine, at a temperature between $-10°$ C. and 25° C.

2-Isothiocyanatopyrimidine (optionally substituted by an alkyl radical) can be prepared by the method described by W. Abraham and G. Barnikow, Tetrahedron, 29, 691 (1973).

2-Isothiocyanatothiophene (optionally substituted by an alkyl radical) can be prepared by the method described by W. C. McCarthy and L. E. Foss, J. Org. Chem., 42, 1,508 (1977).

According to a further feature of the invention, the isoquinoline derivatives of general formula III wherein $A_1$ represents a 3-hydroxymethyl isoquinol-5-yl radical can also be obtained by reducing by methods known per se an ester of the general formula:

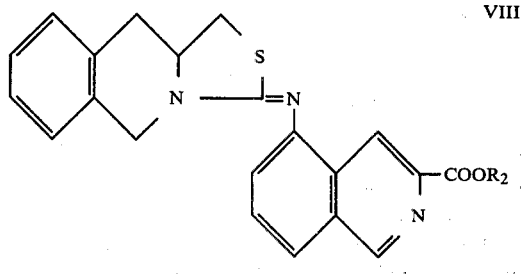

(wherein $R_2$ represents an alkyl radical containing 1 to 4 carbon atoms) to convert the $-COOR_2$ group to a $-CH_2OH$ group.

By the expression methods known per se as used in this specification and the accompanying claims is meant methods heretofore used or described in the chemical literature.

The reduction is preferably carried out by reaction with lithium borohydride prepared in situ, at a temperature between 0° and 20° C., in an organic solvent, such as diglyme, or by reaction with calcium borohydride, prepared in situ, at a temperature of about 20° C., in an organic solvent, such as tetrahydrofuran.

According to a further feature of the invention, the isoquinoline derivatives of general formula III wherein $A_1$ represent a 3-carboxymethylisoquinol-5-yl or 4-(or 5-)carboxyalkylthiazol-2-yl radical optionally substituted by an alkyl radical can also be obtained from the corresponding ester of the general formula:

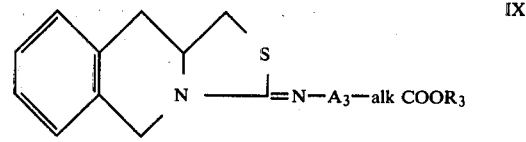

(wherein $R_3$ represents an alkyl radical containing 1 to 4 carbon atoms and either $A_3$ represents an isoquinol-5-yl radical and alk represents a methylene radical in the 3-position, or $A_3$ represents a thiazol-2-yl radical optionally substituted by an alkyl radical as hereinbefore defined and alk represents a linear or branched alkylene radical, containing 1 to 4 carbon atoms, in the 4- or 5-position) by methods known per se for the conversion of an alkoxycarbonyl group to a carboxy group without affecting the rest of the molecule.

The conversion is generally carried out by acid or alkaline hydrolysis, preferably by using hydrochloric acid at a temperature of about 100° C., more preferably in 2 to 4 N aqueous acid, or alternatively by using sodium hydroxide or potassium hydroxide at the reflux temperature of the reaction mixture, preferably in an aqueous or aqueous-alcoholic solution of sodium hydroxide having a concentration of 1 to 5 N.

The compounds of general formulae VIII and IX can be prepared by reacting the corresponding compounds of formulae IV and V in the manner described above for the preparation of isoquinoline derivatives of the general formula III.

When $A_1$ is other than thienyl, the isoquinoline derivatives according to the invention can be converted by methods known per se into addition salts with acids. The acid addition salts can be obtained by reacting the isoquinoline derivatives with acids in a suitable solvent. As organic solvents there may be used alcohols, ketones, ethers or chlorinated hydrocarbons.

When $A_1$ represents a 3-carboxymethylisoquinol-5-yl or 4-(or 5-)carboxyalkylthiazol-2-yl radical optionally substituted by an alkyl radical, the isoquinoline derivatives according to the invention can be converted by methods known per se into metal salts or into addition salts with a nitrogen-containing base. These salts can be obtained by reaction with a metal base (preferably an alkali metal or alkaline earth metal base), ammonia or a nitrogen-containing organic base, in a suitable solvent, such as an alcohol, an ether or water, or by an exchange reaction with a salt of an organic acid.

The salt formed is precipitated, after concentration, if necessary, of its solution and is isolated by filtration or decantation. It is also possible to obtain the salt from its solution in the form of a lyophilisate.

The isoquinoline derivatives of general formula III and their salts, when they exist, can optionally be purified by physical methods, such as crystallisation or chromatography.

The isoquinoline derivatives of general formula III and their pharmaceutically acceptable salts possess useful pharmacological properties. The doses and concentrations referred to below relate to compounds in the (S) form.

They possess an antiviral activity which is effective, in particular, against viruses of the rhinovirus group.

On cell cultures of human MRC-5 fibroblasts infected with human type 1B rhinovirus (R 1112 strain), the isoquinoline derivatives of the invention cause complete inhibition of the cytopathogenic effect and of multiplication of the viruses, at concentrations from 7 to 125 μg/cc (maximum non-cytotoxic concentration) to 0.016 to 30 μg/cc (minimum inhibitory concentration).

Some of the isoquinoline derivatives of general formula III are also valuable analgesic, antipyretic and anti-inflammatory agents.

The anti-inflammatory activity manifests itself in rats at doses between 50 and 200 mg/kg animal body weight, administered orally, using the technique of K. F. Benitz and L. M. Hall, Arch. Int. Pharmacodyn., 144, 185 (1963).

The analgesic activity manifests itself in rats at doses between 20 and 200 mg/kg animal body weight, administered orally, using the technique of E. Siegmund et al., Proc. Soc. Exp. Biol. Med., 95, 729 (1957).

The antipyretic activity manifests itself in rats at doses between 20 and 200 mg/kg animal body weight, administered orally, using the technique of J. J. Loux et al., Toxicol. Appl. Pharmacol., 22, 674 (1972).

Furthermore, the acute toxicity in mice of the isoquinoline derivatives of the invention, expressed as their $LD_{50}$ (50% lethal dose), is between 300 and 900 mg/kg animal body weight or greater than 900 mg/kg animal body weight, administered orally.

In the isoquinoline derivatives of formula III, $A_1$ may represent an isoquinol-8-yl, 3-methylisoquinol-8-yl, 3-hydroxymethylisoquinol-5-yl, 3-carboxymethylisoquinol-5-yl, quinol-5-yl, thienopyrid-3-yl, benzimidazol-5 (or -6)-yl, thien-2-yl, thiazol-2-yl, 1,3,4-thiadiazol-2-yl, pyrazol-3-yl, imidazoyl, pyrimidin-2-yl, pyridazin-3-yl or pyrazin-2-yl radical, it being understood that a monocyclic heterocyclic ring within the definition of $A_1$ may be substituted by a linear or branched alkyl radical containing 1 to 4 carbon atoms and, when $A_1$ is other than thien-2-yl, non-toxic pharmaceutically acceptable acid addition salts thereof and, when $A_1$ represents a 3-carboxymethylisoquinol-5-yl radical, non-toxic pharmaceutically acceptable metal salts thereof and non-toxic pharmaceutically acceptable addition salts thereof with nitrogen-containing bases.

Of particular interest are the isoquinoline derivatives of general formula III wherein $A_1$ represents an isoquinol-8-yl, 3-methylisoquinol-8-yl, 3-hydroxymethylisoquinol-5-yl, quinol-5-yl, thienopyrid-3-yl, benzimidazol-5(or -6)-yl, thien-2-yl or thiazol-2-yl radical, a 4-(or 5-)carboxyalkylthiazol-2-yl radical (wherein the linear or branched alkyl moiety contains 1 to 4 carbon atoms) or a 1,3,4-thiadiazol-2-yl, pyrazol-3-yl, pyrimidin-2-yl, pyridazin-3-yl or pyrazin-2-yl radical, it being understood that monocyclic heterocyclic rings within the definition of $A_1$ may be substituted by a linear or branched alkyl radical containing 1 to 4 carbon atoms, and their salts. Moreover, amongst the preferred isoquinoline derivatives, those which are more especially active are of general formula III wherein $A_1$ represents an isoquinol-8-yl, 3-methylisoquinol-8-yl, 3-hydroxymethylisoquinol-5-yl, quinol-5-yl, thien-2-yl or thiazol-2-yl radical, a 4-carboxyalkylthiazol-2-yl radical (wherein the alkyl moiety contains 1 or 2 carbon atoms), a pyrazol-3-yl radical, a pyrimidin-2-yl radical optionally substituted by a methyl radical, or a pyridazin-3-yl or pyrazin-2-yl radical, and their salts. Preferably the compounds are in the (S) form.

For therapeutic purposes, the isoquinoline derivatives of general formula III are employed as such or in the form of pharmaceutically acceptable salts, i.e. salts containing anions or cations which are relatively innocuous to the animal organism in therapeutic doses of the salts so that the beneficial physiological properties inherent in the isoquinoline derivatives are not vitiated by side-effects ascribable to the anions or cations.

Examples of pharmaceutically acceptable acid addition salts are salts with inorganic acids (such as hydrochlorides, sulphates, nitrates and phosphates) or salts with organic acids (such as acetates, propionates, succinates, benzoates, fumarates, maleates, tartrates, theophillineacetates, salicylates, phenolphthalinates, methylene-bis-β-oxynaphthoates or substituted derivatives of these acids).

The sodium, potassium, calcium, lysine and ethanolamine salts may be mentioned, in particular, as examples of metal salts or addition salts with nitrogen-containing bases.

The following Examples illustrate the preparation of the new isoquinoline derivatives of the present invention.

EXAMPLE 1

A stream of hydrogen sulphide is passed into a solution of bis-(2-aminothiophene hydrochloride) tetrachlorostannate (10 g) in water (500 cc) until the precipitation of tin disulphide has ended. The insoluble material is filtered off. The residual hydrogen sulphide is removed from the filtrate by means of a stream of nitrogen, and the filtrate is then added dropwise to a suspension of (S)-3-methylthio-1,5,10,10a-tetrahydrothiazolo[3,4-b]isoquinolinium iodide (13.7 g) in pyridine (300 cc). After stirring for 17 hours at a temperature of about 20° C., the mixture is concentrated to dryness under reduced pressure (25 mm Hg; 3.3 kPa) at 60° C. The residue is dissolved in a mixture of 2 N sodium hydroxide solution (250 cc) and methylene chloride (250 cc). The organic phase is decanted off, dried over magnesium sulphate, treated with decolorising charcoal and then concentrated to dryness under reduced pressure (40 mm Hg; 5.3 kPa) at 40° C. The residue is dissolved in boiling acetonitrile (100 cc); after cooling to 5° C., the crystals formed are filtered off and washed with ice-cooled acetonitrile (10 cc). After drying at 40° C. under reduced pressure (1 mm Hg; 0.13 kPa), (S)-3-(thien-2-ylimino)-1,5,10,10a-tetrahydrothiazolo[3,4-b]isoquinoline (5.4 g) is obtained in the form of white crystals, m.p.=112° C.

$[\alpha]_D^{20} = -273 \pm 4°$ (c=0.5; chloroform).

Bis-(2-aminothiophene hydrochloride) tetrachlorostannate can be prepared in accordance with the method of W. Steinkopf, reproduced in H. Hartough, The Chemistry of Heterocyclic Compounds: Thiophene and its derivatives, Interscience Publishers (1952), page 513.

EXAMPLE 2

(S)-3-Methylthio-1,5,10,10a-tetrahydrothiazolo[3,4-b]isoquinolinium iodide (18.2 g) is added to a solution of 2-aminothiazole (10.0 g) in pyridine (500 cc). The suspension gradually changes to a solution. After 3 days at a temperature of about 20° C., the mixture is concentrated under reduced pressure (25 mm Hg; 3.3 kPa); the residue is dissolved in a mixture of water (300 cc) and methylene chloride (300 cc). The organic phase is decanted off, dried over magnesium sulphate and filtered and the filtrate is then concentrated to dryness under reduced pressure (25 mm Hg; 3.3 kPa). Propanol (250 cc) is added to the residue; the mixture is heated to the boil and filtered hot. After cooling, the crystals formed are filtered off and washed with propanol (3×10 cc). After drying at 40° C. under reduced pressure (1 mm Hg; 0.13 kPa), the product (11.9 g) obtained is recrystallised from acetonitrile (250 cc). After drying at 60° C. under reduced pressure (0.1 mm Hg; 0.013 kPa), (S)-3-(thiazol-2-ylimino)-1,5,10,10a-tetrahydrothiazolo[3,4-b]isoquinoline (10.6 g) is obtained in the form of white crystals, m.p.=158° C.

$[\alpha]_D^{20} = -235 \pm 2°$ (c=2; chloroform).

EXAMPLE 3

By following the procedure of Example 2, but using (S)-3-methylthio-1,5,10,10a-tetrahydrothiazolo[3,4-b]isoquinolinium iodide (18.2 g) and 2-amino-5-tert.-butyl-1,3,4-thiadiazole (15.7 g) as the starting materials, (S)-3-[(5-tert.-butyl-1,3,4-thiadiazol-2-yl)imino]-1,5,10,10a-tetrahydrothiazolo[3,4-b]isoquinoline (7.0 g) is obtained in the form of white crystals, m.p.=137° C.

$[\alpha]_D^{20} = -203 \pm 2°$ (c=2; chloroform).

2-Amino-5-tert.-butyl-1,3,4-thiadiazole can be prepared in accordance with the method of F. Chubb, Canad. J. Chem., 37, 1,121 (1959).

EXAMPLE 4

By following the procedure of Example 2, but using (S)-3-methylthio-1,5,10,10a-tetrahydrothiazolo[3,4-b]isoquinolinium iodide (18.2 g) and 3-aminopyrazole (8.3 g) as the starting materials, (S)-3-(pyrazol-3-ylimino)-1,5,10,10a-tetrahydrothiazolo[3,4-b]isoquinoline (7.0 g) is obtained in the form of white crystals, m.p.=161° C.

$[\alpha]_D^{20} = -256 \pm 3°$ (c=1; chloroform).

EXAMPLE 5

By following the procedure of Example 2, but using (S)-3-methylthio-1,5,10,10a-tetrahydrothiazolo[3,4-b]isoquinolinium iodide (18.2 g) and 2-amino-4-methylpyrimidine (8.0 g) as the starting materials, (S)-3-[(4-methylpyrimidin-2-yl)imino]-1,5,10,10a-tetrahydrothiazolo[3,4-b]isoquinoline (3.0 g) is obtained in the form of white crystals, m.p.=179° C.

$[\alpha]_D^{20} = -266 \pm 3°$ (c=1; chloroform).

EXAMPLE 6

By following the procedure of Example 2, but using (S)-3-methylthio-1,5,10,10a-tetrahydrothiazolo[3,4-b]isoquinolinium iodide (18.2 g) and 3-aminopyridazine (9.5 g) as the starting materials, (S)-3-(pyridazin-3-ylimino)-1,5,10,10a-tetrahydrothiazolo[3,4-b]isoquinoline (9.3 g) is obtained in the form of light beige crystals, m.p.=140°-142° C.

$[\alpha]_D^{20} = -276 \pm 3°$ (c=2; chloroform).

EXAMPLE 7

By following the procedure of Example 2, but using (S)-3-methylthio-1,5,10,10a-tetrahydrothiazolo[3,4-b]isoquinolinium iodide (16.3 g) and 2-aminopyrazine (8.5 g) as the starting materials, (S)-3-(pyrazin-2-ylimino)-1,5,10,10a-tetrahydrothiazolo[3,4-b]isoquinoline (7.6 g) is obtained in the form of white crystals, m.p.=140° C.

$[\alpha]_D^{20} = -283 \pm 3°$ (c=1; chloroform).

EXAMPLE 8

By following the procedure of Example 2, but using (S)-3-methylthio-1,5,10,10a-tetrahydrothiazolo[3,4-b]isoquinolinium iodide (10.1 g) and 3-aminothieno[2,3-c]pyridine (6.4 g) as the starting materials, (S)-3-[(thieno[2,3-c]pyrid-3-yl)imino]-1,5,10,10a-tetrahydrothiazolo[3,4-b]isoquinoline (6.4 g) is obtained in the form of white crystals, m.p.=180° C.

$[\alpha]_D^{20} = -205 \pm 3°$ (c=1; chloroform)

3-Aminothieno[2,3-c]pyridine can be prepared in accordance with the method of L. H. Klemm, J. Het. Chem., 14, 299 (1977).

EXAMPLE 9

By following the procedure of Example 2, but using (S)-3-methylthio-1,5,10,10a-tetrahydrothiazolo[3,4-b]isoquinolinium iodide (6.7 g) and 3-aminothieno[2,3-b]pyridine (2.8 g) as the starting materials, (S)-3-[(thieno[2,3-b]pyrid-3-yl)imino]-1,5,10,10a-tetrahydrothiazolo[3,4-b]isoquinoline (4.6 g) is obtained in the form of beige crystals, m.p.=145°-146° C.

$[\alpha]_D^{20} = -204 \pm 3°$ (c=0.5; chloroform).

3-Aminothieno[2,3-b]pyridine can be prepared in accordance with the method of L. H. Klemm et al., J. Het. Chem. 7, 373 (1970).

EXAMPLE 10

By following the procedure of Example 2, but using (S)-3-methylthio-1,5,10,10a-tetrahydrothiazolo[3,4-b]isoquinolinium iodide (18 g) and 5(or 6)-aminobenzimidazole hydrochloride (10 g) as the starting materials, (S)-3-[benzimidazol-5(or -6)ylimino]-1,5,10,10a-tetrahydrothiazolo[3,4-b]isoquinoline (11.7 g) is obtained in the form of pink crystals, m.p.=220° C.

$[\alpha]_D^{20} = -236 \pm 3°$ (c=1; methanol).

5(or 6)- Aminobenzimidazole hydrochloride can be prepared in accordance with the method of D. Woolley, J. Biol. Chem., 152, 225 (1944).

EXAMPLE 11

By following the procedure of Example 2, but using (S)-3-methylthio-1,5,10,10a-tetrahydrothiazolo[3,4-b]isoquinolinium iodide (18.2 g) and 8-aminoisoquinoline (10.9 g) as the starting materials, (S)-3-(isoquinol-8-ylimino)-1,5,10,10a-tetrahydrothiazolo[3,4-b]isoquinoline (11.8 g) is obtained in the form of pale yellow crystals, m.p.=206° C.

$[\alpha]_D^{20} = -197 \pm 2°$ (c=1; chloroform).

8-Aminoisoquinoline can be prepared in accordance with the method of D. H. Hey, J. Chem. Soc., 3,882 (1961).

EXAMPLE 12

By following the procedure of Example 2, but using (S)-3-methylthio-1,5,10,10a-tetrahydrothiazolo[3,4-b]isoquinolinium iodide (8 g) and 8-amino-3- methylisoquinoline (3.5 g) as the starting materials, (S)-3-[(3-methylisoquinol-8-yl)imino]-1,5,10,10a-tetrahydrothiazolo[3,4-b]isoquinoline (4.1 g) is obtained in the form of pale yellow crystals, m.p.=156° C.

$[\alpha]_D^{20} = -186 \pm 3°$ (c=1; chloroform).

8-Amino-3-methylisoquinoline can be prepared in the following manner:

A catalyst consisting of palladium-on-carbon (3/97 by weight; 5 g) is added to a solution of 5-bromo-3-methyl-8-nitroisoquinoline (10.8 g) in ethanol (200 cc). The suspension is stirred, whilst heating to the reflux temperature under a nitrogen atmosphere, and hydrazine hydrate (25 cc) is added dropwise in the course of 30 minutes. The mixture is then heated under reflux for a further 2 hours. The suspension is filtered hot through diatomaceous silica and the filtrate is concentrated to dryness under reduced pressure (20 mm Hg; 2.7 kPa) at 40° C. The residue is dissolved in 0.5 N aqueous hydrochloric acid (200 cc) and the resulting solution is extracted with methylene chloride (2×50 cc). The aqueous phase is then rendered alkaline to pH 10 by addition of sodium hydroxide and is extracted with methylene chloride (3×150 cc). The organic extracts are combined, washed with water, dried over magnesium sulphate and filtered and the filtrate is concentrated to dryness under reduced pressure (20 mm Hg; 2.7 kPa) at 40° C. to yield 8-amino-3-methylisoquinoline (4.4 g), which is a beige solid, m.p.=175° C.

5-Bromo-3-methyl-8-nitroisoquinoline can be prepared in the following manner:

5-Bromo-3-methylisoquinoline (17.2 g) is dissolved in sulphuric acid (density: 1.83; 34 N) (100 cc). This solution is stirred and potassium nitrate (8.1 g) is added in the course of 30 minutes, the temperature being kept between 0° and 5° C. by means of an ice bath; the temperature is then allowed to rise to about 20° C. The mixture is stirred for a further 5 hours at this temperature, and the solution is then poured into a water/ice mixture (600 cc), and ammonia solution (density: 0.9) containing 20% of $NH_3$ is added until the pH reaches 10, without exceeding 30° C. The resulting yellow precipitate is filtered off, washed with water, dried and recrystallised from ethanol (300 cc).

After filtration and drying, 5-bromo-3-methyl-8-nitroisoquinoline (12.3 g) is obtained in the form of a beige solid, m.p.=146° C.

5-Bromo-3-methylisoquinoline can be prepared by the method described by M. Gordon et al., J. Het. Chem., 4, 410 (1967).

EXAMPLE 13

By following the procedure of Example 2, but using (S)-3-methylthio-1,5,10,10a-tetrahydrothiazolo-[3,4-b]isoquinolinium iodide (18.2 g) and 5-aminoquinoline (14.4 g) as the starting materials, (S)-3-(quinol-5-yl-imino)-1,5,10,10a-tetrahydrothiazolo[3,4-b]isoquinoline (15.0 g) is obtained in the form of light beige crystals, m.p.=194° C.

$[\alpha]_D^{20} = -195° \pm 2°$ (c=2; Chloroform).

EXAMPLE 14

Lithium chloride (1.01 g), sodium borohydride (0.91 g) and diglyme (diethylene glycol dimethyl ether) (100 cc) are mixed at 0° C. The mixture is stirred for 30 minutes at 0° C. and (S)-3-[(3-methoxycarbonylisoquinol-5-yl)imino]-1,5,10,10a-tetrahydrothiazolo[3,4-b]-isoquinoline (4.7 g) is added. Stirring is continued for 1 hour at 0° C. and then for 2 hours at 20° C. Water (1 liter) is added and the mixture is extracted with methylene chloride (3×150 cc). The organic extracts are combined, washed with water, dried over magnesium sulphate and filtered and the filtrate is concentrated to dryness under reduced pressure (40 mm Hg; 5.3 kPa) at 40° C. The residue is dissolved in methylene chloride (20 cc) and the solution is poured onto a column of diameter 3 cm, containing silica gel (120 g) in methylene chloride. Elution is carried out with an ethyl acetate/cyclohexane mixture (70/30 by volume), 300 cc fractions being collected. Fractions 7 to 11 are combined and concentrated to dryness under reduced pressure (20 mm Hg; 2.7 kPa) at 40° C. The residue is recrystallised from butyl acetate (100 cc). After filtration, washing with diisopropyl ether and drying, (S)-3-[(3-hydroxymethylisoquinol-5-yl)-imino]-1,5,10,10a-tetrahydrothiazolo[3,4-b]isoquinoline (2 g) is obtained, as a white solid, m.p.=210° C.

$[\alpha]_D^{20} = -172° \pm 3°$ (c=0.5; chloroform).

(S)-3-[(3-Methoxycarbonylisoquinol-5-yl)imino]-1,5,10,10a-tetrahydrothiazolo[3,4-b]isoquinoline can be prepared in the following manner:

(S)-3-Methylthio-1,5,10,10a-tetrahydrothiazolo-[3,4-b]isoquinolinium iodide (22.4 g) is added to a solution of 5-amino-3-methoxycarbonylisoquinoline (13 g) in pyridine (400 cc). The suspension gradually changes to a solution. After stirring for 3 days at a temperature of the order of 20° C., the mixture is concentrated to dryness under reduced pressure (20 m Hg; 2.7 kPa) at 60° C. The residue is dissolved in methylene chloride (500 cc) and the solution is washed with a N aqueous sodium hydroxide (3×300 cc) and then with water. The solution is dried over sodium sulphate and filtered and the filtrate is then concentrated to dryness under reduced pressure (20 mm Hg; 2.7 kPa) at 40° C. The residue is recrystallised from acetonitrile (500 cc). After filtration, washing with diisopropyl ether and drying, (S)-3-[(3-methoxycarbonylisoquinol-5-yl)]-imino-1,5,10,10a-tetrahydrothiazolo[3,4-b]-isoquinoline (12.8 g) is obtained, as a pale yellow solid, m.p.=200° C.

5-Amino-3-methoxycarbonylisoquinoline can be prepared in the following manner:

5-Aminoisoquinoline-3-carboxylic acid (25 g) is added to methanol (2 liters). The mixture is heated to the reflux temperature and a stream of dry hydrogen chloride is bubbled through for 3 hours. The mixture is heated under reflux for a further 3 hours and then concentrated to dryness under reduced pressure (20 mm Hg; 2.7 kPa) at 60° C. The residue is dissolved in water (200 cc) and the solution is washed with ethyl acetate (2×100 cc). The aqueous solution is rendered alkaline to pH 9 by adding potassium carbonate. The precipitate formed is filtered off, washed with water and dried to yield 5-amino-3-methoxycarbonylisoquinoline (20.3 g).

5-Aminoisoquinoline-3-carboxylic acid can be prepared in the following manner:

5-Nitroisoquinoline-3-carboxylic acid (44 g) is dissolved in methanol (3 liters), and a catalyst consisting of palladium-on-carbon (3/97 by weight; 15 g) is added. The mixture is hydrogenated at atmospheric pressure, at a temperature between 20° and 25° C. After stirring for 5 hours, the volume of hydrogen absorbed is 13.9 liters. The mixture is filtered through diatomaceous silica and the filtrate is concentrated to dryness under reduced pressure (20 mm Hg; 2.7 kPa) at 60° C. to yield 5-aminoisoquinoline-3-carboxylic acid (35 g).

5-Nitroisoquinoline-3-carboxylic acid can be prepared by the method described by R. C. Elderfield et al., J. Org. Chem., 23, 435 (1958).

EXAMPLE 15

A solution of (S)-3-[(3-ethoxycarbonylmethylisoquinol-5-yl)imino]-1,5,10,10a-tetrahydrothiazolo[3,4-b]-isoquinoline (3.8 g) in 3 N hydrochloric acid (60 cc) is heated at 100° C. for 6 hours. After cooling, the pH of the solution is adjusted to 7 by adding 5 N sodium hydroxide solution, and the mixture is then extracted with methylene chloride (2×200 cc). The organic extracts are combined, dried over magnesium sulphate and then concentrated to dryness. The resulting residue is dissolved in a dimethylformamide/water mixture (2/1 by volume; 60 cc), the solution is heated to the boil, decolorising charcoal (0.3 g) is added and the mixture is filtered hot. After cooling at 5° C. for 20 hours, the crystals which have appeared are filtered off, washed with diisopropyl ether and then dried at 70° C. under reduced pressure (0.1 mm Hg; 0.013 kPa) to yield (S)-3-[(3-carboxymethylisoquinol-5-yl)imino]-1,5,10,10a-tetrahydrothiazolo[3,4-b]isoquinoline (1.7 g), melting at about 200° C. (with decomposition).

$[\alpha]_D^{20} = -152° \pm 2°$ (c=1; chloroform).

(S)-3-[(3-Ethoxycarbonylmethylisoquinol-5-yl)-imino-]-1,5,10,10a-tetrahydrothiazolo[3,4-b]isoquinoline can be prepared in the following manner:

(S)-3-Methylthio-1,5,10,10a-tetrahydrothiazolo-[3,4-b]isoquinolinium iodide (18.5 g) is added to a solution of ethyl 5-aminoisoquinoline-3-acetate (15.8 g) in pyridine (200 cc). After 15 hours at a temperature of the order of 20° C., the solution is concentrated under reduced pressure (25 mm Hg; 3.3 kPa). The residue is dissolved in a mixture of methylene chloride (2 liters) and 5 N sodium hydroxide solution (1 liter). The organic phase is decanted, washed with water (3×1 liter), dried over sodium sulphate and then concentrated to about 100 cc under reduced pressure (25 mm Hg; 3.3 kPa).

This solution is poured onto a column of silica gel (600 g; diameter of the column: 5.5 cm) and elution is then carried out with methylene chloride, 500 cc fractions of eluate being collected. Fractions 18 to 24 are concentrated to dryness; the residue is crystallised from an acetonitrile/diethyl ether mixture (10/50 by volume) to yield (S)-3-[(3-ethoxycarbonylmethylisoquinol-5-yl)imino]-1,5,10,10a-tetrahydrothiazolo-[3,4-b]isoquinoline (9.1 g) in the form of yellow crystals, m.p.=112° C.

$[\alpha]_D^{20} = -146° \pm 2°$ (c=1; chloroform).

Ethyl 5-aminoisoquinoline-3-acetate can be prepared in the following manner:

Ethyl 5-nitroisoquinoline-3-acetate (20 g) is dissolved in ethyl acetate (1 liter), and a catalyst consisting of palladium-on-carbon (3/97 by weight; 21 g) is added. The mixture is hydrogenated at atmospheric pressure, at a temperature of about 50° C., for 2 hours. It is filtered through diatomaceous silica and the filtrate is then concentrated to dryness under reduced pressure (20 mm Hg; 2.7 kPa) at 50° C. to yield ethyl 5-aminoisoquinoline-3-acetate (15.8 g) in the form of beige crystals, m.p.=90° C.

Ethyl 5-nitroisoquinoline-3-acetate can be prepared in the following manner:

A solution of methylene chloride (300 cc) containing ethyl isoquinoline-3-acetate (21.5 g) is poured dropwise into a suspension, cooled to 10° C., of methylene chloride (1,700 cc) containing nitronium trifluoromethanesulphonate prepared in situ by successively adding trifluoromethanesulphonic acid (70 cc) and nitric acid (d=1.52; 23 N) (15.1 cc). The reaction medium is kept at 10° C. for 2 hours and is then allowed to warm up to a temperature of about 20° C.

The mixture is neutralised by adding a solution of sodium carbonate, whilst stirring. The organic phase is decanted off, washed with water (3×1 liter), dried over sodium sulphate and then concentrated to dryness. Purification is carried out by chromatography on silica gel (400 g) contained in a column of diameter 4.5 cm. Elution is carried out successively with methylene chloride (2 liters), a methylene chloride/methanol mixture (98/2 by volume; 2 liters) and a methylene chloride/methanol mixture (96/4 by volume; 4 liters), the eluate being collected in 800 cc fractions. After evaporating fractions 7 to 9 to dryness, ethyl 5-nitroisoquinoline-3-acetate (20 g) is obtained in the form of brown crystals melting at about 90° C.

Ethyl isoquinoline-3-acetate can be prepared in accordance with the method of P. Crooks, J. Med. Chem. 21, 585 (1978).

EXAMPLE 16

5 N Aqueous sodium hydroxide (20 cc) is added to a solution of (S)-3-[(5-ethoxycarbonylmethylthiazol-2-yl)imino]-1,5,10,10a-tetrahydrothiazolo[3,4-b]-isoquinoline (7.9 g) in ethanol (60 cc). The mixture is heated under reflux for two hours. After cooling to 20° C., it is acidified by adding 12 N hydrochloric acid (d=1.19; 10 cc). The resulting precipitate is filtered off and washed with water (3×50 cc) and then with ethanol (50 cc) and diethyl ether (20 cc). The product is recrystallised by dissolving it in dimethylformamide (15 cc) at 70° C., adding ethanol (80 cc) and cooling to 0° C. The resulting crystals are filtered off, washed with ethanol (50 cc) and then with diethyl ether (20 cc) and dried at 50° C. under reduced pressure (0.1 mm Hg; 0.013 kPa) to yield (S)-3-[(5-carboxymethylthiazol-2-yl)imino]-1,5,10,10a-tetrahydrothiazolo[3,4-b]isoquinoline hydrochloride (6.8 g), melting at about 240° C.

$[\alpha]_D^{20} = 301° \pm 4°$ (c=0.5; methanol).

(S)-3-[(5-Ethoxycarbonylmethylthiazol-2-yl)-imino]-1,5,10,10a-tetrahydrothiazolo[3,4-b]isoquinoline can be prepared in the following manner:

(S)-3-Methylthio-1,5,10,10a-tetrahydrothiazolo-[3,4-b]isoquinolinium iodide (10 g) is added to a solution of ethyl (2-aminothiazol-5-yl)acetate (5.1 g) in pyridine (150 cc). After 48 hours at a temperature of the order of 20° C., the solution is concentrated to dryness under reduced pressure (25 mm Hg; 3.3 kPa). The residue is dissolved in a mixture of methylene chloride (200 cc) and N sodium hydroxide solution (100 cc). The organic phase is decanted off, washed with water (3×50 cc), dried over sodium sulphate and then concentrated to dryness under reduced pressure (25 mm Hg; 3.3 kPa) at 40° C. The residue is crystallised by dissolving it in boiling ethanol (100 cc) and cooling to 0° C. The resulting crystals are filtered off, washed with ethanol (30 cc) and diethyl ether (20 cc) and dried at 20° C. under reduced pressure (0.1 mm Hg; 0.013 kPa) to yield (S)-3-[(5-ethoxycarbonylmethylthiazol-2-yl)imino-]-1,5,10,10a-tetrahydrothiazolo[3,4-b]isoquinoline (7.9 g) m.p.=132° C.

Ethyl (2-aminothiazol-5-yl)acetate can be prepared in the following manner:

Thiourea (14.5 g) and ethyl 3-bromo-3-formyl propionate (39.8 g) are mixed in ethanol (250 cc). The mixture is stirred for 20 hours at a temperature of about 20°

C. Gradual dissolution of the reactants is observed. The solution is concentrated to dryness under reduced pressure (25 mm Hg; 3.3 kPa) at 40° C. The residue is dissolved in a mixture of methylene chloride (200 cc) and N sodium hydroxide solution (200 cc). The organic phase is washed with water, dried over magnesium sulphate and filtered and the filtrate is concentrated to dryness under reduced pressure (25 mm Hg; 3.3 kPa) at 40° C. The residue is crystallised by dissolving it in boiling water (150 cc) in the presence of active charcoal (3 g), filtering hot and cooling to 5° C. The resulting crystals are filtered off, washed with water and dried at 20° C. under reduced pressure (0.1 mm Hg; 0.013 kPa) in the presence of phosphorus pentoxide to yield ethyl (2-aminothiazol-5-yl)acetate (7.2 g), m.p. = 101° C.

Ethyl 3-bromo-3-formylpropionate can be prepared by the method of M. Aeberli and H. Erlenmeyer, Helv. Chim. Acta, 33, 503 (1950).

EXAMPLE 17

A 4 N aqueous solution of sodium hydroxide (30 cc) is added to a solution of (S)-3-[(4-ethoxycarbonylmethylthiazol-2-yl)imino]-1,5,10,10a-tetrahydrothiazolo-[3,4-b]isoquinoline (10 g) in ethanol (60 cc). The mixture is heated under reflux for two hours. After cooling to 20° C., it is acidified by adding 12 N hydrochloric acid (d=1.19; 11 cc). The white precipitate which has formed is filtered off, washed with water and dried at 20° C. under reduced pressure (0.1 mm Hg; 0.013 kPa). The resulting solid is crystallised by dissolving it in boiling ethanol (200 cc), cooling and filtering off the crystals formed; the product is then recrystallised by dissolving it in dimethylformamide (60 cc) at 100° C., adding ethanol (120 cc) and cooling to 0° C. The crystals are filtered off, washed with ethanol (20 cc) and then with diethyl ether (20 cc) and dried at 40° C. under reduced pressure (0.1 mm Hg; 0.013 kPa) to yield (S)-3-[(4-carboxymethylthiazol-2-yl)imino]-1,5,10,10a-tetrahydrothiazolo[3,4-b]isoquinoline hydrochloride (5.6 g), m.p. = 206° C.

$[\alpha]_D^{20} = -267° \pm 3°$ (c=1; methanol).

UV spectrum (methanol): λmax=305 nm ($\epsilon$=16,370).

Propylene oxide (0.8 g) is added to a solution of (S)-3-[(4-carboxymethylthiazol-2-yl)imino]-1,5,10,10a-tetrahydrothiazolo[3,4-b]isoquinoline hydrochloride (0.5 g) in methanol (30 cc). The mixture is stirred for 16 hours at a temperature of the order of 20° C. The precipitate which was formed is filtered off and dried under reduced pressure (20 mm Hg; 2.7 kPa) at 40° C. to yield (S)-3-[(4-carboxymethylthiazol-2-yl)imino]-1,5,10,10a-tetrahydrothiazolo[3,4-b]-isoquinoline (0.2 g), which is a white solid, m.p. = 185° C.

(S)-3-[(4-Carboxymethylthiazol-2-yl)imino]-1,5,10,10a-tetrahydrothiazolo[3,4-b]isoquinoline sodium salt can be prepared in the following manner:

0.1 N Sodium hydroxide solution (5 cc) is added to a stirred suspension of (S)-3-[(4-carboxymethyl-thiazol-2-yl)imino]-1,5,10,10a-tetrahydrothiazolo-[3,4-b]isoquinoline (0.17 g) in water (10 cc). The resulting solution is filtered in order to remove a small amount of insoluble material, and the filtrate is concentrated to dryness under reduced pressure (20 mm Hg; 2.7 kPa) at 60° C. The resulting white solid is dried under reduced pressure (0.1 mm Hg; 0.013 kPa) at 60° C. to yield the sodium salt of (S)-3-[(4-carboxymethylthiazol-2-yl)imino]-1,5,10,10a-tetrahydrothiazolo[3,4-b]-isoquinoline (0.17 g).

UV spectrum (water): λmax=305 nm ($\epsilon$=12,300).

(S)-3-[(4-Ethoxycarbonylmethylthiazol-2-yl)imino]-1,5,10,10a-tetrahydrothiazolo[3,4-b]isoquinoline can be prepared in the following manner:

(S)-3-Methylthio-1,5,10,10a-tetrahydrothiazolo[3,4-b]isoquinolinium iodide (18.1 g) is added to a solution of ethyl (2-aminothiazol-4-yl)acetate (10 g) in pyridine (300 cc). After 48 hours at a temperature of the order of 20° C., the solution is concentrated to dryness under reduced pressure (25 mm Hg; 3.3. kPa) at 60° C. The residue is dissolved in a mixture of methylene chloride (200 cc) and N sodium hydroxide solution (100 cc). The organic phase is decanted off, washed with water (3×100 cc), dried over sodium sulphate and then concentrated to dryness under reduced pressure (25 mm Hg; 3.3 kPa) at 40° C. The residue is recrystallised by dissolving it in boiling acetonitrile (100 cc) and then cooling. The crystals formed are filtered off, washed with acetonitrile (20 cc) and then with diethyl ether (20 cc) and dried at 20° C. under reduced pressure (0.1 mm Hg; 0.013 kPa) to yield (S)-3-[(4-ethoxycarbonylmethylthiazol-2-yl)imino]-1,5,10,10a-tetrahydrothiazolo[3,4-b]isoquinoline (11.7 g), m.p. = 105° C.

Ethyl (2-aminothiazol-4-yl)acetate can be prepared in accordance with the method described by M. Steude, Liebigs Ann. Chem., 261, 22 (1891).

EXAMPLE 18

5 N Aqueous sodium hydroxide (20 cc) is added to a solution of (S)-3-{[4-(4-methoxycarbonylbutyl)-thiazol-2-yl]imino}-1,5,10,10a-tetrahydrothiazolo[3,4-b]-isoquinoline (7.4 g) in ethanol (60 cc). The mixture is heated under reflux for 2 hours. After cooling to 20° C., it is acidified by adding 12 N hydrochloric acid (d=1.19; 10 cc). Diethyl ether (30 cc) is added and the mixture is cooled to 0° C. The resulting precipitate is filtered off, washed with water (4×15 cc), ethanol (2×10 cc) and diethyl ether (2×30 cc) and crystallised by dissolving it in boiling propan-2-ol (200 cc) and cooling to 0° C. The resulting crystals are filtered off, washed with propan-2-ol (20 cc) and diethyl ether (50 cc) and dried at 45° C. under reduced pressure (0.1 mm Hg; 0.013 kPa) to yield (S)-3-{[4-(4-carboxybutyl)-thiazol-2-yl]imino}-1,5,10,10a-tetrahydrothiazolo[3,4-b]isoquinoline hydrochloride (4.9 g), m.p. = 214° C.

$[\alpha]_D^{20} = -226° \pm 3°$ (c=1; methanol).

(S)-3-{[4-(4-Methoxycarbonylbutyl)thiazol-2-yl]imino}-1,5,10,10a-tetrahydrothiazolo[3,4-b]isoquinoline can be obtained in the following manner:

(S)-3-Methylthio-1,5,10,10a-tetrahydrothiazolo[3,4-b]isoquinolinium iodide (10 g) is added to a solution of methyl 5-(2-aminothiazol-4-yl)valerate (5.9 g) in pyridine (150 cc). After 48 hours at a temperature of the order of 20° C., the solution is concentrated to dryness under reduced pressure (25 mm Hg; 3.3 kPa) at 60° C. The residue is stirred in a mixture of methylene chloride (250 cc) and N sodium hydroxide solution (100 cc).

The insoluble product is filtered off, washed with water and then with ethanol and recrystallised by dissolving it in boiling ethanol (100 cc) and cooling to 0° C. The resulting crystals are filtered off, washed with ethanol (20 cc) and diethyl ether (20 cc) and dried at 20° C. under reduced pressure (0.1 mm Hg; 0.013 kPa) to yield (S)-3-{[4-(4-methoxycarbonylbutyl)thiazol-2-yl]imino}-1,5,10,10a-tetrahydrothiazolo[3,4-b]isoquinoline (7.4 g), as a white solid, m.p. = 92° C.

Methyl 5-(2-aminothiazol-4-yl)valerate can be prepared in the following manner:

Thiourea (15.7 g) and methyl 7-chloro-6-oxoheptanoate (39.7 g) are mixed in ethanol (200 cc). The mixture is stirred for 20 hours at a temperature of about 20° C.; gradual dissolution of the reactants is observed. The solution is concentrated to dryness under reduced pressure (25 mm Hg; 3.3 kPa) at 40° C. The residue is stirred in a mixture of methylene chloride (250 cc) and N sodium hydroxide solution (250 cc). The insoluble product is filtered off, washed with water and recrystallised by dissolving it in boiling water (350 cc) and cooling to 5° C. The resulting crystals are washed with water (3×30 cc), ethanol (3×30 cc) and diethyl ether (2×50 cc) and dried at 20° C. under reduced pressure (0.1 mm Hg; 0.013 kPa) to yield methyl 5-(2-aminothiazol-4-yl)valerate (31 g), as a white solid, m.p.=131° C.

Methyl 7-chloro-6-oxoheptanoate can be prepared in accordance with the method described in Belgian Pat. No. 867,128.

EXAMPLE 19

5 N Aqueous sodium hydroxide (20 cc) is added to a solution of (10a-S)-3-{[4-(1-ethoxycarbonylethyl)-thiazol-2-yl]imino}-1,5,10,10a-tetrahydrothiazolo-[3,4-b]isoquinoline (8.2 g) in ethanol (60 cc). The mixture is heated under reflux for two hours. After cooling to 20° C., it is acidified by adding 12 N hydrochloric acid (d=1.19; 10 cc). Diethyl ether (30 cc) is added and the mixture is cooled to 0° C. The resulting precipitate is filtered off, washed with water and then with ethanol and recrystallised from boiling ethanol (80 cc). After cooling, the resulting crystals are washed with ethanol and dried at 50° C. under reduced pressure (0.1 mm Hg; 0.013 kPa). This yields (10a-S)-3-{[4-(1-carboxyethyl)-thiazol-2-yl]imino}-1,5,10,10a-tetrahydrothiazolo[3,4-b]isoquinoline hydrochloride (3.8 g), melting at about 200°–210° C.

$[\alpha]_D^{20} = -234° \pm 3°$ (c=0.5; methanol).

(10a-S)-3-{[4-(1-Ethoxycarbonylethyl)thiazol-2-yl]imino}-1,5,10,10a-tetrahydrothiazolo[3,4-b]-isoquinoline can be prepared in the following manner:

(S)-3-Methylthio-1,5,10,10a-tetrahydrothiazolo-[3,4-b]isoquinolinium iodide (10 g) is added to a solution of ethyl 2-(2-aminothiazol-4-yl)propionate (5.5 g) in pyridine (150 cc). After 48 hours at a temperature of about 20° C., the solution is concentrated to dryness under reduced pressure (25 mm Hg; 3.3 kPa). The residue is dissolved in a mixture of methylene chloride (100 cc) and N sodium hydroxide solution (100 cc). The organic phase is decanted off, washed with water (3×50 cc), dried over sodium sulphate and then concentrated to dryness under reduced pressure (25 mm Hg; 3.3 kPa) at 40° C. to yield (10a-S)-3-{[4-(1-ethoxycarbonylethyl)-thiazol-2-yl]imino}-1,5,10,10a-tetrahydrothiazolo[3,4-b]isoquinoline (8.2 g) in the form of a yellow oil.

Ethyl 2-(2-aminothiazol-4-yl)propionate can be prepared by the method described by R. G. Woodbridge and G. Dougherty, J. Amer. Chem. Soc., 71, 1,744 (1949).

EXAMPLE 20

5 N Aqueous sodium hydroxide (20 cc) is added to a solution of (S)-3-[(5-methoxycarbonylmethyl-4-methylthiazol-2-yl)imino]-1,5,10,10a-tetrahydrothiazolo[3,4-b]isoquinoline (8.1 g) in ethanol (60 cc). The mixture is heated under reflux for two hours. After cooling to 20° C., it is acidified by adding 12 N hydrochloric acid (d=1.19; 10 cc). The resulting precipitate is filtered off, washed with water (5×25 cc), ethanol (3×15 cc) and diethyl ether (2×25 cc) and recrystallised by dissolving it in dimethylformamide (80 cc) at 150° C. and cooling to 0° C. The resulting crystals are filtered off, washed with dimethylformamide (10 cc), ethanol (4×15 cc) and diethyl ether (3×15 cc) and dried at 45° C. under reduced pressure (0.1 mm Hg; 0.013 kPa) to yield (S)-3-[(5-carboxymethyl-4-methylthiazol-2-yl)imino]-1,5,10,10a-tetrahydrothiazolo[3,4-b]-isoquinoline hydrochloride (4.8 g), as a white solid melting at about 250° C.

$[\alpha]_D^{20} = -293° \pm 3°$ (c=0.5; methanol).

(S)-3-[(5-Methoxycarbonylmethyl-4-methylthiazol-2-yl)imino]-1,5,10,10a-tetrahydrothiazolo[3,4-b]isoquinoline can be obtained in the following manner:

(S)-3-Methylthio-1,5,10,10a-tetrahydrothiazolo-[3,4-b]isoquinolinium iodide (10 g) is added to a solution of ethyl (2-amino-4-methylthiazol-5-yl)acetate (5.5 g) in pyridine (150 cc). After 48 hours at a temperature of the order of 20° C., the solution is concentrated to dryness under reduced pressure (25 mm Hg; 3.3 kPa) at 60° C. The residue is dissolved in a mixture of methylene chloride (200 cc) and N sodium hydroxide solution (100 cc). The organic phase is washed with water (2×100 cc), dried over magnesium sulphate and filtered and the filtrate is concentrated to dryness under reduced pressure (25 mm Hg; 3.3 kPa) at 40° C. The residue is crystallised by dissolving it in boiling ethanol (120 cc) and cooling to 0° C. The resulting crystals are filtered off, washed with ethanol (30 cc) and diethyl ether (20 cc) and dried at 20° C. under reduced pressure (0.1 mm Hg; 0.013 kPa) to yield (S)-3-[(5-methoxycarbonylmethyl-4-methylthiazol-2-yl)imino]-1,5,10,10a-tetrahydrothiazolo[3,4-b]-isoquinoline (8.1 g), as a white solid, m.p.=66° C.

Ethyl (2-amino-4-methylthiazol-5-yl)acetate can be prepared by the method described by H. Yasuda, J. Sci. Research Inst. (Tokyo), 51, 32 (1957).

The present invention includes within its scope pharmaceutical compositions comprising, as active ingredient, at least one of the compounds of general formula III in the (S) form, or a non-toxic salt thereof, in association with a pharmaceutically acceptable carrier or adjuvant. The invention includes especially such preparations made up for intranasal, oral, rectal, parenteral or topical administration.

Solid compositions for oral administration include tablets, pills, powders (preferably contained in gelatin capsules) and granules. In such solid compositions the active compound is admixed with at least one inert diluent such as sucrose, lactose or starch. The compositions may also comprise, as in normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as liquid paraffin. Besides inert diluents such compositions may also comprise adjuvants, such as wetting, emulsifying and suspending agents, and sweetening, flavouring and aromatizing agents. The compositions according to the invention for oral administration include capsules of absorbable material such as gelatin containing the active substance with or without the addition of diluents or excipients, e.g. as powders.

Preparations according to the invention for nasal or parenteral administration include sterile aqueous or non-aqueous solutions, suspensions or emulsions. Examples of non-aqueous solvents or vehicles are propylene glycol, polyethylene glycol, vegetable oils (in particular olive oil, almond oil or coconut oil), and injectable organic esters such as ethyl oleate. These compositions may also contain adjuvants such as preserving, wetting, emulsifying and dispersing agents (e.g soya lecithin). They may be sterilized by, for example, filtration through a bacteria-retaining filter, by incorporation in the compositions of sterilizing agents, by irradiation, by heating, or by the addition of a preservative. They may also be manufactured in the form of sterile solid compositions which can be dissolved in a sterile injectable medium immediately before use.

Compositions for rectal administration are suppositories which contain, in addition to the active substance, excipients such as cacao butter or a suitable wax base, e.g. a semi-synthetic glyceride.

Compositions for topical administration can be, for example, in the form of ointments.

The percentage of active ingredient in the compositions of the invention may be varied, it being necessary that is should constitute a proportion such that a suitable dosage shall be obtained.

The compositions according to the invention are particularly useful in human therapy by virtue of their antiviral action. They are indicated, in particular, for the treatment of viral infections of the respiratory tract.

In human therapy, the doses of the isoquinoline derivative(s) depend on the desired effect and the duration of the treatment. For an adult, they are generally between 100 and 2000 mg per day, administered orally. They can reach 100 mg per day when administered nasally (drops or sprays).

In general, the physician will decide the posology considered appropriate, taking into account the age, weight and other factors peculiar to the patient being treated.

The following Examples illustrate pharmacological compositions according to the invention.

EXAMPLE 21

Tablets containing a 100 mg dose of active product and having the following composition are prepared in accordance with the usual technique:

| | |
|---|---|
| (S)-3-(pyridazin-3-ylimino)-1,5,10,10a-tetrahydrothiazolo[3,4-b]isoquinoline | 0.100 g |
| starch | 0.110 g |
| precipitated silica | 0.035 g |
| magnesium stearate | 0.005 g |

EXAMPLE 22

Tablets containing a 100 mg dose of active product and having the following composition are prepared in accordance with the technique below:

| | |
|---|---|
| (S)-3-[(4-carboxymethylthiazol-2-yl)-imino]-1,5,10,10a-tetrahydrothiazolo-[3,4-b]isoquinoline | 0.100 g |
| wheat starch | 0.137 g |
| dicalcium phosphate | 0.040 g |
| sodium salt of carboxymethylstarch | 0.015 g |
| magnesium stearate | 0.008 g |

The active product, the dicalcium phosphate and about 90% of the starch are mixed and then passed through a sieve (mesh size: 0.5 mm). A 10% paste prepared from the remaining starch is added, the resulting paste is converted to granules by passing it through a sieve (mesh size: 0.8 mm) and the granules are dried in an oven at about 50° C. The sodium salt of carboxymethylstarch and the magnesium stearate are then added and the mixture is compressed to form tablets.

EXAMPLE 23

A 1% w/v oily solution for intranasal administration is prepared by dissolving (S)-3-(thiazol-2-ylimino)-1,5,10,10a-tetrahydrothiazolo[3,4-b]-isoquinoline (1 g) in olive oil (100 cc) at 40°–50° C., and filtering the resulting solution through a Millipore filter. For administration, the solution is applied to the nasal mucous membrane by means of a dropper.

EXAMPLE 24

A 1% w/v aqueous solution of active product for intranasal administration is prepared by dissolving the sodium salt of (S)-3-[4-carboxymethylthiazol-2-yl)-imino]-1,5,10,10a-tetrahydrothiazolo[3,4-b]isoquinoline (1.07 g) in distilled water (100 cc). For administration, the solution is applied to the nasal mucous membrane by means of a dropper.

It will be appreciated that the pharmaceutical compositions of the invention may comprise, in addition to the (S) compound of general formula III, a quantity of the compound of general formula III in the (R) form. For example the compound used to prepare the compositions may be in the (R,S) form. Provided that the composition comprises an effective amount of the (S) compound the composition may also comprise a further quantity of the (R) compound as an adjuvant. Preferably however, the compound of formula III in the composition is in the (S) form.

We claim:

1. An isoquinoline derivative of the formula:

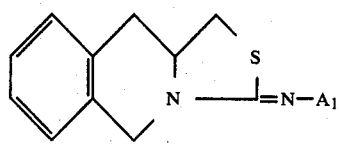

III wherein the symbol $A_1$ represents an isoquinol-8-yl, 3-methylisoquinol-8-yl, 3-hydroxymethylisoquinol-5-yl, 3-carboxymethylisoquinol-5-yl, quinol-5-yl, thienopyrid-3-yl, benzimidazol-5(or -6)-yl, thien-2-yl or thiazol-2-yl radical, a 4-(or 5-) carboxyalkylthiazol-2-yl radical in which the alkyl moiety is linear or branched and contains 1 to 4 carbon atoms, or a 1,3,4-thiadiazol-2-yl, pyrazol-3-yl, imidazolyl, pyrimidin-2-yl, pyridazin-3-yl or pyrazin-2-yl radical, it being understood that a monocyclic heterocyclic ring within the definition of $A_1$ may be substituted by a linear or branched alkyl radical containing 1 to 4 carbon atoms, in the (S) or (R,S) form or a mixture thereof, or when $A_1$ is other than thien-2-yl, a non-toxic pharmaceutically acceptable acid addition salt thereof, or, when $A_1$ represents a 3-carboxymethylisoquinol-5-yl or 4-(or 5-)-carboxyalkylthiazol-2-yl radical, optionally substituted by an alkyl radical as hereinbefore defined, a non-toxic pharmaceutically acceptable metal salt thereof or a non-toxic pharmaceutically acceptable addition salt thereof with a nitrogen-containing base.

2. An isoquinoline derivative according to claim 1 wherein $A_1$ represents an isoquinol-8-yl, 3-methylisoquinol-8-yl, 3-hydroxymethylisoquinol-5-yl, 3-carboxymethylisoquinol-5-yl, quinol-5-yl, thienopyrid-3-yl, benzimidazol-5(or -6)-yl, thien-2-yl, thiazol-2-yl, 1,3,4-thiadiazol-2-yl, pyrazol-3-yl, imidazolyl, pyrimidin-2-yl, pyridazin-3-yl or pyrazin-2-yl radical, it being understood that a monocyclic heterocyclic ring within the definition of $A_1$ may be substituted by a linear or branched alkyl radical containing 1 to 4 carbon atoms or, when $A_1$ is other than thien-2-yl, a non-toxic pharmaceutically acceptable acid addition salt thereof or, when $A_1$ represents a 3-carboxymethylisoquinol-5-yl radical, a non-toxic pharmaceutically acceptable metal salt thereof or a non-toxic pharmaceutically acceptable addition salt thereof with a nitrogen-containing base.

3. An isoquinoline derivative according to claim 1 wherein $A_1$ represents an isoquinol-8-yl, 3-methylisoquinol-8-yl, 3-hydroxymethylisoquinol-5-yl, quinol-5-yl, thienopyrid-3-yl, benzimidazol-5(or -6)-yl, thien-2-yl or thiazol-2-yl radical, a 4-(or 5-) carboxyalkylthiazol-2-yl radical (wherein the linear or branched alkyl moiety contains 1 to 4 carbon atoms) or a 1,3,4-thiadiazol-2-yl, pyrazol-3-yl, pyrimidin-2-yl, pyridazin-3-yl or pyrazin-2-yl radical, it being understood that a monocyclic heterocyclic ring within the definition of $A_1$ may be substituted by a linear or branched alkyl radical containing 1 to 4 carbon atoms or, when $A_1$ is other than thien-2-yl, a non-toxic pharmaceutically acceptable acid addition salt thereof, or, when $A_1$ represents a 4-(or 5-) carboxyalkylthiazol-2-yl radical, a non-toxic pharmaceutically acceptable metal salt thereof or a non-toxic pharmaceutically acceptable addition salt thereof with a nitrogen-containing base.

4. An isoquinoline derivative according to claim 1 wherein $A_1$ represents an isoquinol-8-yl, 3-methylisoquinol-8-yl, 3-hydroxymethylisoquinol-5-yl, quinol-5-yl, thien-2-yl or thiazol-2-yl radical, a 4-carboxyalkylthiazol-2-yl radical (wherein the alkyl moiety contains 1 or 2 carbon atoms), a pyrazol-3-yl radical, a pyrimidin-2-yl radical optionally substituted by a methyl radical, or a pyridazin-3-yl or pyrazin-2-yl radical or, when $A_1$ is other than thien-2-yl, a non-toxic pharmaceutically acceptable acid addition salt thereof or, when $A_1$ represents a 4-carboxyalkylthiazol-2-yl radical, a non-toxic pharmaceutically acceptable metal salt thereof or a non-toxic pharmaceutically acceptable addition salt thereof with a nitrogen-containing base.

5. A compound according to claim 1 in the (S)-form.

6. A compound according to claim 1 which is (S)-3-(pyridazin-3-ylimino)-1,5,10,10a-tetrahydrothiazolo-[3,4-b]isoquinoline or a non-toxic pharmaceutically acceptable acid addition salt thereof.

7. A compound according to claim 1 which is (S)-3-[(4-carboxymethylthiazol-2-yl)imino]-1,5,10,10a-tetrahydrothiazolo[3,4-b]isoquinoline, a non-toxic pharmaceutically acceptable acid addition salt thereof, a non-toxic pharmaceutically acceptable metal salt thereof, or a non-toxic pharmaceutically acceptable addition salt thereof with a nitrogen-containing base.

8. A compound according to claim 1 which is (S)-3-(thiazol-2-ylimino)-1,5,10,10a-tetrahydrothiazolo-[3,4-b]-isoquinoline or a non-toxic pharmaceutically acceptable acid addition salt thereof.

9. A compound according to claim 1 which is (S)-3-[(5-tert-butyl-1,3,4-thiadiazol-2-yl)imino]-1,5,10,10a-tetrahydrothiazolo[3,4-b]isoquinoline, (S)-3-(pyrazol-3-ylimino)-1,5,10,10a-tetrahydrothiazolo-[3,4-b]-isoquinoline, (S)-3-[(4-methylpyrimidin-2-yl)imino]-1,5,10,10a-tetrahydrothiazolo[3,4-b]isoquinoline, (S)-3-(pyrazin-2-ylimino)-1,5,10,10a-tetrahydrothiazolo-[3,4-b]-isoquinoline, (S)-3-[(thieno[2,3-c]pyrid-3-yl)-imino]-1,5,10,10a-tetrahyrothiazolo[3,4-b]isoquinoline, (S)-3-[(thieno[2,3-b]pyrid-3-yl)imino]-1,5,10,10a-tetrahydrothiazolo[3,4-b]isoquinoline, (S)-3-[benzimidazol-5(or -6)-ylimino]-1,5,10,10a-tetrahydrothiazolo[3,4-b]-isoquinoline, (S)-3-(isoquinol-8-ylimino)-1,5,10,10a-tetrahydrothiazolo[3,4-b]isoquinoline, (S)-3-[(3-methylisoquinol-8-yl)imino]-1,5,10,10a-tetrahydrothiazolo[3,4-b]-isoquinoline, (S)-3-(quinol-5-ylimino)-1,5,10,10a-tetrahydrothiazolo[3,4-b]isoquinoline, (S)-3-[(3-hydroxymethylisoquinol-5-yl)imino]-1,5,10,10a-tetrahydrothiazolo[3,4-b]-isoquinoline or a non-toxic pharmaceutically acceptable acid addition salt thereof, (S)-3-[(3-carboxymethylisoquinol-5-yl)imino]-1,5,10,10a-tetrahydrothiazolo[3,4-b]-isoquinoline, a non-toxic pharmaceutically acceptable acid addition salt thereof, a non-toxic pharmaceutically acceptable metal salt thereof or a non-toxic pharmaceutically acceptable addition salt thereof with a nitrogen-containing base, or (S)-3-(thien-2-ylimino)-1,5,10,10a-tetrahydrothiazolo[3,4-b]isoquinoline.

10. A compound according to claim 1 which is (S)-3-[(5-carboxymethylthiazol-2-yl)imino]-1,5,10,10a-tetrahydrothiazolo[3,4-b]isoquinoline, (S)-3-{[4-(4carboxybutyl)thiazol-2-yl]imino}-1,5,10,10a-tetrahydrothiazolo-[3,4-b]isoquinoline, (10a-S)-3-{[4-(1-carboxyethyl)thiazol-2-yl]imino}-1,5,10,10a-tetrahydrothiazolo[3,4-b]-isoquinoline, (S)-3-[(5-carboxymethyl-4-methylthiazol-2-yl)imino]-1,5,10,10a-tetrahydrothiazolo-[3,4-b]isoquinoline, a non-toxic pharmaceutically acceptable acid addition salt thereof, a non-toxic pharmaceutically acceptable metal salt thereof or a non-toxic pharmaceutically acceptable addition salt thereof with a nitrogen-containing base.

* * * * *